United States Patent [19]

Fitz, Jr.

[11] Patent Number: 5,326,554

[45] Date of Patent: Jul. 5, 1994

[54] ORAL COMPOSITIONS FOR TREATING PLAQUE AND GINGIVITIS

[75] Inventor: Thomas E. Fitz, Jr., Loveland, Ohio

[73] Assignee: The Procter & Gamble Company, Cincinnati, Ohio

[21] Appl. No.: 52,316

[22] Filed: Apr. 23, 1993

[51] Int. Cl.$^5$ ............... A61K 7/16; A61K 7/18
[52] U.S. Cl. ........................ 424/49; 424/52
[58] Field of Search ................. 424/49-58

[56] References Cited

U.S. PATENT DOCUMENTS

| | | | |
|---|---|---|---|
| 4,144,322 | 3/1979 | Cordon et al. | 424/49 |
| 4,174,387 | 11/1979 | Cordon et al. | 424/52 |
| 4,367,218 | 1/1983 | Jacobson | 424/49 |
| 4,657,758 | 4/1987 | Goldemberg et al. | 424/49 |
| 4,666,708 | 5/1987 | Goldemberg et al. | 424/49 |
| 4,891,211 | 1/1990 | Winston | 424/52 |
| 4,925,655 | 5/1990 | Smigel et al. | 424/52 |
| 5,004,597 | 4/1991 | Majeti et al. | 424/52 |
| 5,041,280 | 8/1991 | Smigel | 424/52 |
| 5,145,666 | 9/1992 | Lukacovic et al. | 424/52 |
| 5,192,532 | 3/1993 | Guay et al. | 424/53 |
| 5,213,790 | 5/1993 | Lukacovic et al. | 424/52 |

*Primary Examiner*—Shep K. Rose
*Attorney, Agent, or Firm*—Douglas C. Mohl; David K. Dabbiere; Jacobus C. Rasser

[57] ABSTRACT

Disclosed are oral compositions which provide a pleasant feel to the mouth and have improved stability.

4 Claims, No Drawings

ORAL COMPOSITIONS FOR TREATING PLAQUE AND GINGIVITIS

TECHNICAL FIELD

The present invention relates to oral compositions which provide a pleasant feel to the mouth and exhibit improved stability. Oral care products containing a bicarbonate salt have achieved a significant level in certain markets of the world such as the U.S. The users of bicarbonate products indicate that their mouths feel refreshed after using such a product. References disclosing bicarbonate containing compositions include: U.S. Pat. Nos. 3,935,305; 3,927,321; 3,937,804; 3,943,240; 4,623,536; 4,721,614; 4,547,362; and 4,663,153, all incorporated herein by reference.

Although bicarbonate products have been disclosed, there is a continuing need to develop improved products. The present inventors have found that the inclusion of sodium carbonate as a buffer improves the stability of the products.

It is therefore an object of the present invention to provide improved products containing a bicarbonate salt.

It is a further object of the present invention to provide more effective products containing sodium bicarbonate.

It is still a further object to provide methods for refreshing the oral cavity.

These and other objects will become readily apparent from the disclosure which follows.

All percentages and ratios used herein are by weight unless otherwise specified. Also, all measurements referred to herein are made at 25° C. in the composition unless otherwise specified.

SUMMARY OF THE INVENTION

The present invention, in certain aspects, embraces compositions containing a bicarbonate salt and sodium carbonate.

The present invention also encompasses a method for refreshing the oral cavity using the specified compositions.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

DETAILED DESCRIPTION OF THE INVENTION

The present invention in a certain aspect involves forming an aqueous composition containing a bicarbonate salt and sodium carbonate. The essential and optional components of the compositions are set forth in detail below.

Bicarbonate Salt

An essential component of the present invention is a bicarbonate salt. The preferred bicarbonate salt is sodium bicarbonate which is a staple item of commerce. The bicarbonate is used at a level of from about 5% to about 70%, preferably from about 10% to about 40%.

Sodium Carbonate

A second essential component of the present invention is sodium carbonate. This material serves as a buffer and helps to stabilize the compositions. This material is used at a level of from about 0.25% to about 2%, preferably from about 0.5% to about 1.5%.

Water

Water is also present in the compositions of this invention. Water employed in the preparation of commercially suitable compositions should preferably be deionized and free of organic impurities. Water generally comprises from about 10% to 50%, preferably from about 20% to 40%, by weight of the toothpaste compositions herein while mouthwashes contain from about 40% to about 95%, preferably 50% to 80%. These amounts of water include the free water which is added plus that which is introduced with other materials as with sorbitol.

Optional Components

The compositions of the present invention may contain an addition to the above-listed components many others which will be somewhat dependent on the type of composition (mouthwashes, toothpastes, topical gels, prophylaxis pastes and the like). Toothpastes and mouthwashes are the preferred systems with toothpastes being the most preferred.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename "Zeodent" particularly the silica carrying the designation "Zeodent 110". These silica abrasives are described in U.S. Pat. No. 4,340,583, Jul. 29, 1982, incorporated herein by reference.

The abrasive in the dentifrice compositions described herein is present at a level of from about 6% to about 70%, preferably from about 15% to about 30% when the dentifrice is a toothpaste.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cylclamate. Flavoring and sweetening agents are generally used in the compositions herein at levels of from about 0.005% to about 2% by weight.

In preparing toothpastes, it is necessary to add some thickening material to provide a desirable consistency. Preferred thickening agents are carboxyvinyl polymers, carrageenan, hydroxy-ethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Thickening agents in a combined amount from 0.5% to 5.0% by weight of the total composition may be used.

Surfactants are also useful in the compositions of this invention and include many different types of materials. Suitable surfactants include any which are reasonably stable and function over a wide pH range. Included are non-soap anionic, nonionic, cationic, zwitterionic and amphoteric organic synthetic surfactants. Many of these are disclosed by Gieseke et al. in U.S. Pat. No. 4,051,234, Sep. 27, 1988 incorporated herein in total by reference.

It is also desirable to include a humectant in a toothpaste to keep it from hardening. Suitable humectants include glycerin, sorbitol, and other edible polyhydric alcohols at a level of from about 10% to about 70%.

Another preferred embodiment of the present invention is a mouthwash composition. Mouthwashes generally comprise from about 20:1 to about 2:1 of a water-/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant(s), 0% to 2% (preferably 0.01% to 0.15%) emulsifying agent, 0% to 0.5% (preferably 0.005% to 0 06%) sweetening agent such as saccharin, 0% to 0.3% (preferably from 0.03% to 0.3%) flavoring agent, and the balance water.

The pH of the present compositions and/or its pH in the mouth can be any pH which is safe for the mouth's hard and soft tissues. Such pH's are generally from about 5 to about 10, preferably from about 8.5 to about 9.5. This latter pH range is the range in which the neat product pH preferably falls.

Another optional component of the compositions of this invention is an anionic polycarboxylate. The anionic polymeric polycarboxylates optionally but preferably employed herein are well known, being employed in the form of their free acids or partially or preferably fully neutralized water soluble alkali metal (e.g. preferably sodium) or ammonium salts. Preferred are 1:4 to 4:1 copolymers of maleic anhydride or acid with another polymerizable ethylenically unsaturated monomer, preferably methyl vinyl ether methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, incorporated herein by reference, include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic toohomers include vinylacetate, vinyl chloride, dimethyl maleate and the like. Copolymers contain sufficient carboxylic salt groups for water-solubility.

Also useful herein are carboxyvinyl polymers, referred to herein earlier as suitable binders, disclosed as toothpaste components in U.S. Pat. Nos. 3,980,767 issued Sep. 14, 1976 to Choun et al., 3,935,306 issued Jan. 27, 1976 to Roberts et al., 3,919,409 issued Nov. 11, 1975 to Peria et al., 3,911,904 issued Oct. 7, 1975 to Harrison, and 3,711,604 issued Jan. 16, 1973 to Colodney et al. They are commercially available for example under the trademarks Carbopol 934, 940, 941 and 956 of B.F. Goodrich, these products consisting essentially of a colloidally water-soluble polymer of polyacrylic acid crosslinked with from about 0.75% to about 2.0% of polyallyl sucrose or polyallyl pentaerythritol as cross-linking agent.

The synthetic anionic polymeric polycarboxylate component is mainly a hydrocarbon with optional halogen and O-containing substituents and linkages as present in for example ester, ether and OH groups, and when present is generally employed in the instant compositions in approximate weight amounts of 0.05 to 3%, preferably 0.05 to 2%, more preferably 0.1 to 2%.

Another optional component is a fluoride ion source. The sources of fluoride ions, or fluoride-providing compounds, useful according to this invention are well known in the art as anticaries agents and pyrophosphatase inhibitors and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, barium fluoride, sodium fluorsilicate, ammonium fluorosilicate, sodium fluorozirconate, sodium monofluorophosphate, aluminum mono- and difluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluoride-providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), an amount of such compound which releases up to about 5,000 ppm of $F^-$ ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

Other anticalculus agents are metal ions such as zinc disclosed in U.S. Pat. No. 4,022,880, May 10, 1977 to Vinson incorporated herein by reference. Still others are polymers such as those described in U.S. Pat. No. 4,661,341, Apr. 28, 1987 to Benedict and U.S. Pat. No. 3,429,963, Feb. 25, 1969 to Shedlovsky, both of which are incorporated herein by reference. Such metals are used in an amount of from about 0.01% to about 5%, preferably about 0.1% to about 2%, while such polymers are used in amounts of from about 0.1% to about 10%, preferably from about 0.5% to about 5%.

Still other anticalculus agents are pyrophosphate salts such as di- and tetra-alkali metal pyrophosphates and others disclosed in U.S. Pat. No. 4,999,184, Mar. 12, 1991, to Parran et al., incorporated herein by reference.

Other optional components for use in the present compositions are non-cationic water insoluble agents such as triclosan. Such materials are disclosed in U.S. Pat. No. 4,022,899 to Vinson et al., incorporated herein by reference.

Method of Manufacture

The compositions of the present invention can be prepared using the method described following the Examples.

Composition Use

The present invention in its method aspect involves applying to the oral cavity safe and effective amounts of the composition. Generally, amounts of at least about 1 gram of the composition is effective.

Given below are examples representative of the present invention. They describe and demonstrate preferred embodiments within the invention's scope.

The examples are given solely for the purpose of illustration and are not to be construed as limitations of this invention. Many variations thereof are possible without departing from the invention's spirit and scope.

EXAMPLE I

Given below is a dentifrice representative of the present invention:

| Material | Paste Wt. % | Gel Wt. % |
|---|---|---|
| Sorbitol | 40.040 | 40.240 |
| Bicarbonate | 20.000 | 20.000 |
| Silica | 15.000 | 15.000 |
| Water | 10.000 | 10.000 |
| Glycerin | 7.000 | 7.000 |
| SASS | 4.000 | 4.000 |
| Carbonate | 1.000 | 1.000 |
| Flavor | 1.000 | 1.000 |
| CMC | 0.850 | 0.850 |
| Saccharin | 0.517 | 0.517 |
| Ti02 | 0.350 | 0.000 |
| Fluoride | 0.243 | 0.243 |
| Blue Dye | 0.000 | 0.150 |
| Totel | 100.000 | 100.000 |

EXAMPLE II

Given below is another dentifrice representative of the present invention.

| Material | Paste Wt. % |
|---|---|
| Water | 20.334 |
| Glycerin | 19.000 |
| Sodium bicarbonate | 17.000 |
| Silica | 16.000 |
| Sorbitol (70%) | 8.951 |
| Tetrasodium pyrophosphate | 7.644 |
| Sodium lauryl sulfate (27.9%) | 4.000 |
| PEG-6 | 3.000 |
| Sodium carbonate | 1.250 |
| Flavor | 1.000 |
| Carboxymethylcellulose | 0.700 |
| Sodium saccharin | 0.528 |
| Titanium dioxide | 0.350 |
| FD&C Blue No. 1 | — |
| Sodium fluoride | 0.243 |
| | 100.000 |

What is claimed is:

1. Aqueous dentifrice toothpaste gel or cream consisting essentially of about 5% to about 70% of bicarbonate salt, from about 0.25% to about 2% of sodium carbonate, from about 10% to about 50% water, and from about 6% to about 70% of a silica dental abrasive which does not excessively or unduly abrade tooth enamel or dentin.

2. A composition according to claim 1 wherein said bicarbonate salt is sodium bicarbonate.

3. A process for cleaning the oral cavity by applying to said cavity an effective amount of a composition according to claim 1.

4. A process for cleansing the oral cavity by applying to said cavity an effective amount of a composition according to claim 2.

* * * * *